United States Patent [19]

Gorun et al.

[11] Patent Number: 5,025,101
[45] Date of Patent: Jun. 18, 1991

[54] NOVEL TETRANUCLEAR MANGANESE COMPLEXES

[75] Inventors: Sergiu M. Gorun, Upper Montclair; Robert T. Stibrany, Long Valley, both of N.J.

[73] Assignee: Exxon Research & Engineering Company, Florham Park, N.J.

[21] Appl. No.: 541,699

[22] Filed: Jun. 21, 1990

[51] Int. Cl.$^5$ ............................................. C07F 13/00
[52] U.S. Cl. ........................................ 556/50; 556/49
[58] Field of Search ................................... 556/49, 50

[56] References Cited

U.S. PATENT DOCUMENTS

| | | | |
|---|---|---|---|
| 4,352,751 | 10/1982 | Wieder et al. | 556/50 |
| 4,730,066 | 3/1988 | White | 556/50 |
| 4,746,507 | 5/1988 | Quag | 556/50 X |
| 4,965,211 | 10/1990 | Wieder et al. | 556/50 X |

Primary Examiner—Arthur C. Prescott
Attorney, Agent, or Firm—Joseph J. Dvorak

[57] ABSTRACT

Briefly stated, the present invention comprises a composition of matter having the formula:

$$M_2[Mn_4(O)(OH)(O_2CR)_2L_2]$$

wherein M is an alkali earth metal selected from magnesium, calcium, strontium, barium or mixtures thereof, R is hydrogen or a hydrocarbyl group, and L is a ligand having the formula:

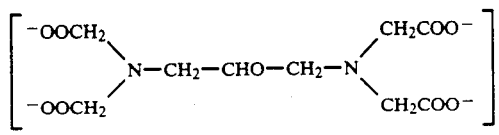

The present invention also encompasses methods for preparing these novel compounds.

12 Claims, 1 Drawing Sheet

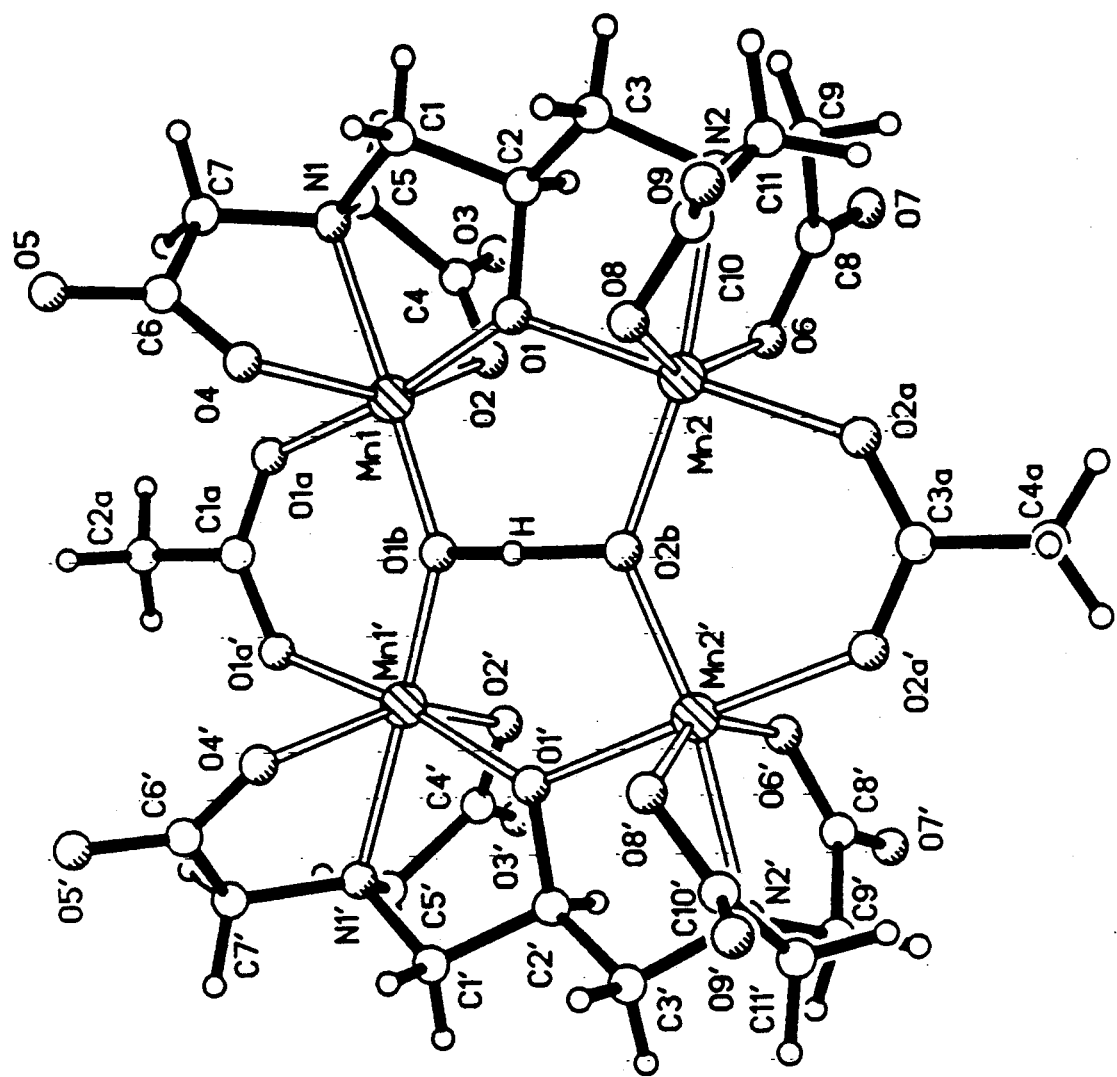

NOVEL TETRANUCLEAR MANGANESE COMPLEXES

FIELD OF THE INVENTION

This invention relates to a new class of compounds. More specifically, it relates to compounds having an oxo (hydroxo) bridged tetranuclear manganese core and to their method of preparation.

BACKGROUND OF THE INVENTION

For information on the plethora of known oxo bridged tetranuclear manganese compounds, reference is made to the following review articles: K. Wieghardt, *Angew. Chem. Int. Ed. English*, 28, p. 1153 (1989); J. B. Vincent, G. Christou, *Adv. Inorg. Chem.*, 33, p. 197 (1989); G. Christou, *Acc. Chem. Res.*, 22, p. 328 (1989); and G. W. Brudvig, R. H. Crabtree, *Prog. Inorg. Chem.*, 37, p. 99 (1989). As can be deduced from these articles, the manganese in these compounds appear in various oxidation states, spatial arrangements and the like. Importantly, none of the compounds reported have the unique core of the novel compounds of the present invention.

More recently, a sodium salt of a valence delocalized oxo bridged tetranuclear manganese compound was reported by W. H. Armstrong et al at the 199th ACS National Meeting. A portion of that report is included in the printed abstracts of the meeting. (See Abstract of Papers, Part 1, 199th ACS National Meeting, Apr. 22-27, 1990, Abstract No. 397.) Importantly, the compounds of the present invention are distinguishable from the compounds reported at that meeting.

SUMMARY OF THE INVENTION

Accordingly, we have now discovered a new class of valence trapped oxo (hydroxo) bridged tetra nuclear manganese compounds. Thus, briefly stated, the present invention comprises a composition of matter having the formula:

wherein M is an alkali earth metal selected from magnesium, calcium, strontium, barium or mixtures thereof, R is hydrogen or a hydrocarbyl group, and L is a ligand having the formula:

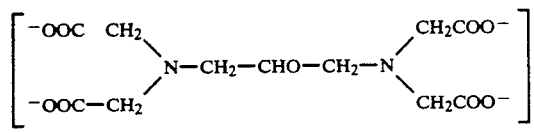

Preferably, in the above composition R is a hydrocarbyl group, such as an alkyl group, having from 1 to about carbon atoms and, more preferably, an alkyl group having from 1 to about 10 carbon atoms. When R is an aralkyl group, it preferably will have from 7 to about carbon atoms.

Another embodiment of the present invention comprises a method of preparing a compound having the formula:

where M, L and R are the same as listed above, which method comprises combining an aqueous solution of a compound having the formula:

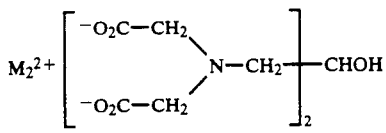

wherein M is magnesium, calcium, strontium, barium or a mixture thereof with a manganese (II) carboxylate, $Mn(O_2CR)_2$, or a water soluble manganese (II) salt and a source of carboxylate, $RCO_2^-$, wherein R is hydrogen or a hydrocarbyl group, and thereafter adding a source of oxygen, such as air, oxygen, and hydrogen peroxide in amounts and for a time sufficient to form a compound having the formula:

The compounds of the present invention have particular suitability for use in decomposition of peroxides.

BRIEF DESCRIPTION OF THE DRAWINGS

The sole figure in the instant application illustrates the oxo (hydroxo) bridged tetranuclear manganese core for one novel compound, $M_2[Mn_4(O)(OH)(O_2CCH_3)_2L_2]$, of the present invention.

DETAILED DESCRIPTION OF THE INVENTION

The compounds of the present invention have the formula:

in which M is an alkaline earth metal selected from Mg, Ca, Sr, Ba or mixtures thereof, R is hydrogen or a hydrocarbyl group, especially alkyl, aryl and aralkyl groups. Preferably, R is an alkyl group having from to about 30 carbon atoms and, more preferably, R has from 1 to about 10 carbon atoms; and when R is an aralkyl group, it preferably will have from 7 to about 10 carbon atoms.

In the above formula, L is a ligand having the formula:

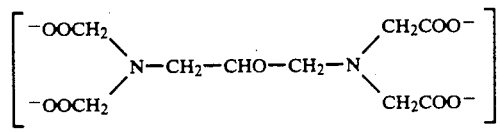

As is shown in the accompanying figure, these novel compounds have a core structure of four manganese atoms which are bridged by oxo and hydroxo groups and, hence, these compounds are referred to as oxo (hydroxo) bridged tetranuclear manganese compounds. Additionally, the compounds of the present invention are valence trapped, in contrast to valence delocalized tetranuclear compounds. The concept of valence trapped and valence delocalized compounds is discussed, for example, in *Advances in Inorganic Chemistry*, Vol. 10, p. 150, Academic Press (1967). Suffice it to say that each of the manganese ions in the compounds of the present invention are deemed to have an integer valence state and, hence, are valence trapped. Compounds in which the manganese ions are believed to have fractional valence states are called valence delocalized.

The structure of the compounds of the present invention have been determined by well known single crystal x-ray diffraction techniques.

The compounds of the present invention are prepared by combining an aqueous containing solution of a compound having the formula:

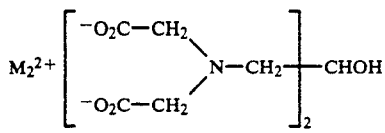

$$M_2^{2+} \left[ \begin{array}{c} ^-O_2C-CH_2 \\ ^-O_2C-CH_2 \end{array} \!\!\!\!\!\! N-CH_2-CHOH \right]_2 \qquad \text{I}$$

in which M is magnesium, calcium, strontium, barium or mixtures thereof, with manganese (II) carboxylate, $Mn(O_2CR)_2$, or a water soluble manganese (II) salt and a source of carboxylate, $RCO_2^-$, in which R is hydrogen or a hydrocarbyl group and thereafter oxidizing the mixture to form the compounds of the invention. Examplary hydrocarbyl groups for R include alkyl groups, aryl groups and aralkyl groups, and when R is an alkyl group, in general it will have from 1 to about 30 carbon atoms and, preferably, from 1 to 10 carbon atoms. When R is an aralkyl group, it generally will have from about 7 to about 10 carbon atoms.

Exemplary manganese (II) salts suitable for use in the present invention include manganese chloride, manganese bromide, manganese nitrate, manganese tetrafluoroborate and manganese sulfate.

Exemplary sources of carboxylate include carboxylic acids and alkali metal salts of carboxylic acids.

Among suitable aqueous containing solutions are water, water-alcohol and water-dimethyl formamide mixtures. In general, it is particularly preferred to use water as the solvent.

The molar ratio of compound I to manganese (II) carboxylate or manganese (II) salt generally will be in the range of from about 1:1 to about 1:3 and preferably about 1:2.

Because the acid analog of compound I is commercially available, it is particularly preferred in the practice of the present invention to prepare an aqueous containing solution of compound I by first neutralizing an aqueous solution of the acid analog with an alkaline earth metal hydroxide or mixture thereof, and thereafter adding the manganese (II) carboxylate or manganese (II) salt and source of carboxylate.

As pointed out above, this aqueous mixture is then oxidized. This is achieved by adding an oxidant such as air, molecular oxygen, or hydrogen peroxide. When air or oxygen is employed, they can be bubbled through the mixture in an amount sufficient to form the desired compound. When hydrogen peroxide is used as the oxidant, in general the peroxide will have a concentration range of about 10 wt.% to 30 wt.% and, preferably, about 25 wt.%. The addition of hydrogen peroxide to the reaction mixture results in an exothermic reaction and consequently it is particularly preferred to maintain the temperature of the reaction mixture during oxidation in the range of about ° C. to 60° C. and, preferably, in the range of about 20° C. to 40° C. In contrast, when air or oxygen is used as the oxidant, the mixture may be heated up to about 60° C. and, preferably, in the range of from about 20° C. to 40° C.

Also, because the compounds of the present invention are excellent peroxide decomposers, when hydrogen peroxide is used as the oxidant, it is preferred to use excess hydrogen peroxide; for example, up to a about 10 times the stoichiometric amount required.

Typically, the desired compound is recovered by fractional crystallization from suitable solvents such as water-dimethyl formamide mixtures.

Use of various manganese compounds as peroxide decomposers, bleach activators and the like are disclosed in the exemplary publications referenced below:

U.S. Pat. No. 3,019,197
U.S. Pat. No. 3,156,654
U.S. Pat. No. 3,398,096
U.S. Pat. No. 3,882,223
U.S. Pat. No. 3,884,836
U.S. Pat. No. 4,119,557
U.S. Pat. No. 4,427,490
U.S. Pat. No. 4,508,700
U.S. Pat. No. 4,536,183
U.S. Pat. No. 4,620,935
U.S. Pat. No. 4,626,373
U.S. Pat. No. 4,626,374
U.S. Pat. No. 4,631,141
U.S. Pat. No. 4,731,161
U.S. Pat. No. 4,776,856

The compounds of the present invention share similar utility to those listed above. Indeed, the compounds of the present invention are particularly suitable as hydrogen peroxide decomposers. For example, the compounds of this invention are more catalytically active than, for example, manganese (II) chloride, manganese (III) tetraphenyl porphirin acetate, manganese (II) acetate. In one series of tests, for example, the rate of oxygen evolution from a hydrogen peroxide solution was measured using equimolar amounts of each of the foregoing compounds as peroxide decomposers. The compounds of this invention were at least one order of magnitude more active than manganese (II) chloride, manganese (III) tetraphenyl porphirin acetate, and manganese (II) acetate.

EXAMPLES

In the examples which follow, DHPTA refers to 1,3-diamino-2-hydroxypropane-N,N,N'N'-tetraacetic acid.

EXAMPLE 1

Preparation of $(Ba,Ca)_2[Mn_4(O)(OH)(O_2CCH_3)L_2]$

To 15 ml of $H_2O$, 268 mg (0.83 mmol) of DHPTA was added and the pH was brought to 7.0 with an equimolar amount of $Ba(OH)_2$ and $Ca(OH)_2$. After adding 406 mg (1.66 mmol) of $Mn(O_2CCH_3)_2 \cdot 4H_2O$ dissolved in 1 ml methanol, the pH of the stirred solution was brought to 8.5 with an equimolar amount of $Ba(OH)_2$ and $Ca(OH)_2$. Addition of 1 ml of (25%) $H_2O_2$ generated heat and gas evolution and the solution became dark brown. A crystalline decahydrate of $(Ca,Ba)_2[Mn_4(O)(OH)(O_2CCH_3)L_2]$ is obtained upon addition of dimethyl formamide (DMF) followed by slow evaporation of the mixture.

Chemical Analysis: $C_{26}H_{33}N_4O_{22}(Ba,Ca)_2Mn_4 \cdot 10\text{-}H_2O$ Calc'd (Observed) %: Ca: 2.94 (2.99); C: 22.93 (22.70); H: 3.85 (3.79); N: 4.11 (4.19).

The single crystals, 0.3×0.3×0.6 mm, were monoclinic, space group P21/m (No. 11), a=11.203(2), b=20.506(4), c=11.741(2)Å, $\beta$=98.12(1)0, V=2670(1)Å³, Z=2; Nicolet difractometer, graphite monochromator, Mo$_k\alpha$ radiation.

EXAMPLE 2

Preparation of (Ba,Ca)$_2$[Mn$_4$(O)(OH)(O$_2$CCH$_3$)$_2$L$_2$]

In a 100 ml round-bottom flask, 268 mg of DHPTA was added to 20 ml of H$_2$O. This was brought to pH 7.0 using a 1:1 mole mixture of Ba(OH)$_2$ and Ca(OH)$_2$. Then, 420 mg of Mn(O$_2$CCH$_3$)$_2$·4H$_2$O in 1 ml MeOH was added and kept stirring. The pH was adjusted to 8.0 with the Ba(OH)$_2$:Ca(OH)$_2$. The mixture was heated to 40° C. with a heating mantle while air was bubbled through the solution. After 15 minutes, the solution became dark red brown, 2.5 ml of DMF was added, the solution was filtered and set to crystallize in a beaker. Microcrystals formed. An IR of the solid is identical to that of the material formed in Example 1.

EXAMPLE 3

Preparation of Ba$_2$[Mn$_4$(O)(OH)(O$_2$C(CH$_2$)$_3$CH$_3$)L$_2$]

268 mg of DHPTA was placed in a 50 ml flask, to which 10 ml H$_2$O was then added. The pH of the solution was brought to 6 using Ba(OH)$_2$. Then 477 mg of Mn(NO$_3$)$_2$·6H$_2$O was added to the solution, followed by 750 mg of valeric acid. Next, the pH of the mixture was brought to 8.5 with Ba(OH)$_2$, after which 1 ml of 25% H$_2$O$_2$ was added, giving off heat and oxygen. The solution became dark red brown. 3 ml DMF was added, the mixture was filtered and set to crystallize in a beaker by evaporation. The product has an infrared spectrum similar to the product from Example 1.

EXAMPLE 4

Preparation of Ba$_2$[Mn$_4$(O)(OH)(O$_2$C(CH$_2$)$_4$CH$_3$)$_2$L$_2$]

The method of Example 3 was followed, except hexanoic acid was substituted for valeric acid.

EXAMPLE 5

Preparation of Ca$_2$[Mn$_4$(O)(OH)(O$_2$CCH$_3$)$_2$L$_2$]

268 mg DHPTA was added with 10 ml H$_2$O to a 50 ml flask. The solution was brought to pH 8 with powdered Ca(OH)$_2$. In another flask, 445 mg of Mn(O$_2$CCH$_3$)$_2$·4H$_2$O was dissolved in 10 ml of 1:1 H$_2$O:MeOH. Then 200 mg of CaCl$_2$ was also dissolved in the Mn(O$_2$CCH$_3$)$_2$ solution. Next, the manganese containing solution was added to the DHPTA solution and stirred for 5 minutes. The pH was adjusted to 8.0 with Ca(OH)$_2$, after which ½ ml of 30% H$_2$O$_2$ was added dropwise. Finally, 4 ml of DMF was added, the solution was filtered and set to crystallize by evaporation in a 100 ml beaker. X-ray diffraction analysis of the product showed it to be isomorphous with the product from Example 1.

EXAMPLE 6

Preparation of Ba$_2$[Mn$_4$(O)(OH)(O$_2$CCH$_3$)$_2$L$_2$]

In a 50 ml flask containing 5 ml of H$_2$O, 100 mg of Ba(OH)$_2$ was neutralized with concentrated HCl to pH7. Then 445 mg of Mn(O$_2$CCH$_3$)$_2$·4H$_2$O was added, along with 10 ml of 1:1 H$_2$O/MeOH. In another 50 ml flask, 268 mg of DHPTA was added to 10 ml of H$_2$O. This was neutralized with solid Ba(OH)$_2$ while stirring. The two solutions were mixed together and stirred about 10 minutes, after which the pH was adjusted to 8.0 using Ba(OH)$_2$ solid. Next, ½ ml of 30% H$_2$O$_2$ was added dropwise. Then 5 ml of DMF was added, stirred 10 minutes, filtered and set to crystallize by evaporation.

The solution evaporated to about ½ of the original volume and crystals formed.

EXAMPLE 7

Preparation of Mg$_2$[Mn$_4$(O)(OH)(O$_2$CCH$_3$)$_2$L$_2$]

Mg(OH)$_2$ was prepared by adding excess MgCl$_2$ to a NaOH solution. The white solid Mg(OH)$_2$ was collected by filtration and washed once with H$_2$O . In a 50 ml round-bottom flask, 268 mg of DHPTA was placed with 5 ml H$_2$O . This was dissolved and brought to a pH of 8 with the Mg(OH)$_2$ prepared above. In a separate 50 ml flask, 445 mg of Mn(O$_2$CCH$_3$)$_2$·4H$_2$O and 200 mg of MgCl$_2$·6H$_2$O was dissolved in 5 ml H$_2$O and 5 ml MeOH. The manganese containing solution was added to the DHPTA solution. Then 1 ml of 30% H$_2$O was added dropwise to the mixture, after which 4 ml DMF was added. The mixture was stirred 5 minutes, filtered and set to crystallize in a beaker by evaporation. Small wellformed crystals were obtained, which had a morphology similar to the product obtained in Example 5. Also, x-ray analysis was obtained, indicating the same tetranuclear core structure.

EXAMPLE 8

Preparation of Ba$_2$[Mn$_4$(O)(OH)(CH$_3$CO$_2$)$_2$L$_2$]

In a 50 ml flask containing 10 ml H$_2$O, 268 mg of DHPTA was added and brought to pH 7 with Ba(OH)$_2$. Then 477 mg of Mn(NO$_3$)$_2$·6H$_2$O was added and stirred for 10 minutes. Next, 700 mg of acetic anhydride was added and the pH was brought to 8.5 with Ba(OH)$_2$. To this mixture 1 ml of 25% H$_2$O$_2$ was added dropwise. Then 4 ml DMF was added, the solution was filtered and set to crystallize by evaporation. The crystals which formed were very dark red, nearly cubic with dimensions 0.25 mm³ to 0.3 mm³.

What is claimed is:

1. A composition of matter having the formula:

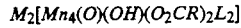

wherein

M is Mg, Ca, Sr, Ba or mixtures thereof,

R is hydrogen or a hydrocarbyl group; and,

L is a ligand having the formula:

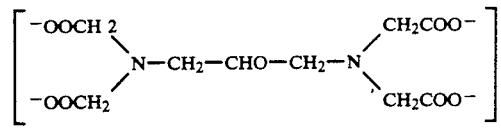

2. The composition of claim 1 wherein R is a hydrocarbyl group selected from alkyl, aryl and aralkyl groups.

3. The composition of claim 2 wherein R is an alkyl group having from 1 to about 30 carbon atoms.

4. The composition of claim 3 wherein R has from 1 to about 10 carbon atoms.

5. A method of preparing a compound having the formula:

wherein

M is Mg, Ca, Sr, Ba or mixtures thereof,

R is hydrogen or a hydrocarbyl group; and,
L is a ligand having the formula:

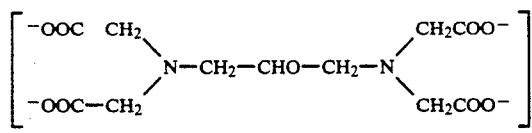

comprising:
combining an aqueous containing solution of a first compound of the formula:

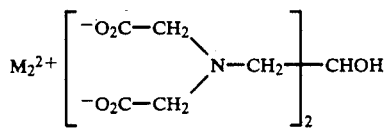

in which M is magnesium, calcium, strontium, barium or mixtures thereof, with manganese (II) carboxylate, $Mn(O_2CR)_2$, or a water soluble manganese (II) salt and a source of carboxylate, $^-O_2CR$, in which R is hydrogen or a hydrocarbyl group, and thereafter adding an oxidant in an amount and for a time sufficient to form the compound.

6. The method of claim 5 wherein the oxidant is selected from air, oxygen and $H_2O_2$.

7. The method of claim 6 wherein the oxidant is an aqueous solution containing from about 10 wt.% to about 30 wt.% $H_2O_2$.

8. The method of claim 6 wherein the temperature is maintained between about ° C. and 60° C. during addition of the oxidant.

9. The method of claim 6 wherein manganese (II) carboxylate is combined with the solution of the first compound.

10. The method of claim 6 wherein a water soluble manganese (II) salt and source of carboxylate are combined with the solution of the first compound.

11. The method of claim 10 wherein the source of carboxylate is a carboxylic acid.

12. The method of claim 11 wherein the acid is neutralized with a base.

* * * * *